United States Patent
Lockemeyer

(12) 
(10) Patent No.: US 6,656,874 B2
(45) Date of Patent: *Dec. 2, 2003

(54) PROCESS FOR PREPARING CATALYSTS WITH IMPROVED CATALYTIC PROPERTIES

(75) Inventor: John Robert Lockemeyer, Sugarland, TX (US)

(73) Assignee: Shell Oil Company, Houston, TX (US)

(*) Notice: Subject to any disclaimer, the term of this patent is extended or adjusted under 35 U.S.C. 154(b) by 195 days.

This patent is subject to a terminal disclaimer.

(21) Appl. No.: 09/805,317

(22) Filed: Mar. 13, 2001

(65) Prior Publication Data

US 2002/0010094 A1 Jan. 24, 2002

Related U.S. Application Data

(63) Continuation of application No. 09/392,522, filed on Sep. 9, 1999, now abandoned
(60) Provisional application No. 60/100,195, filed on Sep. 14, 1998.

(51) Int. Cl.$^7$ ................................................ B01J 23/50
(52) U.S. Cl. ................ 502/347; 502/344; 502/348; 502/300; 502/325; 502/302; 502/216; 502/208; 502/202; 502/224
(58) Field of Search ................ 502/344, 347, 502/348, 300, 340, 325, 337, 338, 339, 302, 216, 208, 202, 224

(56) References Cited

U.S. PATENT DOCUMENTS

| | | | | |
|---|---|---|---|---|
| 3,895,093 A | * | 7/1975 | Weidenbach et al. | 423/213.5 |
| 4,235,798 A | * | 11/1980 | Bartley et al. | 502/241 |
| 4,244,889 A | * | 1/1981 | Bartley et al. | 564/132 |
| 4,368,144 A | * | 1/1983 | Mitsuhata et al. | 502/348 |
| 4,420,420 A | * | 12/1983 | Mita et al. | 502/261 |
| 4,665,048 A | * | 5/1987 | Van Leeuwen et al. | 502/221 |
| 4,994,587 A | * | 2/1991 | Notermann et al. | 549/534 |
| 5,187,140 A | * | 2/1993 | Thorsteinson et al. | 502/348 |
| 5,703,253 A | * | 12/1997 | Evans et al. | 549/536 |
| 5,739,075 A | * | 4/1998 | Matusz | 502/302 |
| 5,935,894 A | * | 8/1999 | Kanazirev | 502/341 |
| 6,281,160 B1 | * | 8/2001 | Basset et al. | 502/332 |
| 6,368,998 B1 | * | 4/2002 | Lockemeyer | 502/347 |

* cited by examiner

*Primary Examiner*—Tom Dunn
*Assistant Examiner*—Christina Ildebrando

(57) ABSTRACT

This invention relates to a process for depositing one or more catalytically reactive metals on a carrier, said process comprising selecting a carrier and depositing a catalytically effective amount of one or more catalytically reactive metals on the carrier, the deposition effected by submersing the carrier in an impregnation solution wherein the hydrogen ion activity of the impregnation solution has been lowered. The invention further relates to catalysts made from the process.

25 Claims, No Drawings

US 6,656,874 B2

PROCESS FOR PREPARING CATALYSTS WITH IMPROVED CATALYTIC PROPERTIES

This application is a continuation of Ser. No. 09/392,522, filed Sep. 9, 1999, now abandoned, which claims the benefit of Provisional application Ser. No. 60/100,195, filed Sep. 14, 1998.

FIELD OF THE INVENTION

The invention relates to a process for the preparation of catalysts with improved catalytic properties, particularly improved initial activity, initial selectivity and/or activity and/or selectivity performance over time.

BACKGROUND OF THE INVENTION

Numerous methods are known for the deposition of catalytically reactive metals on a carrier in order to manufacture catalysts. For example, U.S. Pat. No. 3,972,829, issued Aug. 3, 1976, discloses a method for distributing catalytically reactive metallic components on carriers using an impregnating solution of catalyst precursor compound and an organic thioacid or a mercaptocarboxylic acid. U.S. Pat. No. 4,005,049, issued Jan. 25, 1977, teaches the preparation of a silver/transition metal catalyst useful in oxidation reactions. International publication WO 96/23585, published Aug. 8, 1996, teaches that boosting the amount of alkali metal promoter in a silver solution results in improved properties.

Literature also warns against certain methods. U.S. Pat. No. 4,908,343, issued Mar. 13, 1990, warns against having a silver solution which has a strong acidity or basicity as the strongly acid or base solution would leach any leachable impurities from the carrier, becoming part of the silver catalyst in amounts which adversely affects the performance of the catalyst in an oxidation reaction.

It has surprisingly been found that the metal deposition and catalytic properties of a catalyst may be greatly improved by lowering the hydrogen ion activity of the impregnation solution.

SUMMARY OF THE INVENTION

According to one embodiment of the invention, there is provided a process for depositing one or more catalytically reactive metals on a carrier, said process comprising:
  selecting a carrier; and
  depositing a catalytically effective amount of one or more catalytically reactive metals on said carrier, said deposition effected by an impregnating solution wherein a hydrogen ion activity of said impregnation solution is lowered.

There is further provided a process for preparing a catalyst suitable for the vapor phase production of epoxides, said process comprising:
  selecting a carrier; and
  depositing a catalytically effective amount of silver on the carrier, wherein said deposition is effected by an impregnation solution wherein a hydrogen ion activity of said impregnation solution is lowered.

There is still further provided catalysts made by the processes of the embodiments herein described.

DESCRIPTION OF THE PREFERRED EMBODIMENTS

It has been found that lowering the hydrogen ion activity of the impregnation solution used to deposit catalytically reactive metals on a carrier provides catalysts which have improved catalytic properties, such as activity, selectivity and the activity and/or selectivity performance over time. The process is believed to work to improve the properties of most catalysts wherein metal is deposited on a carrier by use of an impregnation solution.

Catalysts are commonly made by depositing a catalytically effective amount of one or more catalytically reactive metals on a carrier to make a catalyst precursor. Typically, the carrier is impregnated with metal or compound(s), complex(es) and/or salt(s) sufficient to deposit or impregnate the catalytically reactive material. As used herein, "catalytically effective amount" means an amount of metal that provides a measurable catalytic effect.

The impregnated carrier, or catalyst precursor, is dried in the presence of an atmosphere which also reduces the catalytic metal. Drying methods known in the art include steam drying, drying in an atmosphere with a controlled oxygen concentration, drying in reducing atmospheres, air drying, and staged drying using a suitable ramped or staged temperature curve.

In the process of the invention, improvement in the catalytic properties are seen when the metal deposition is effected by use of an impregnation solution whose hydrogen ion activity has been lowered. "Hydrogen ion activity" as used herein is the hydrogen ion activity as measured by the potential of a hydrogen ion selective electrode. As used herein, a solution with "lowered" hydrogen ion activity refers to a solution whose hydrogen activity has been altered by the addition of a base, such that the hydrogen ion activity of the altered solution is lowered compare to the hydrogen ion activity of the same solution in an unaltered state. The base selected to alter the solution may be chosen from any base or compound with a pKb lower an the original impregnation solution. It is particularly desirable to choose a base which does not alter the formulation of the impregnation solution; i.e., which does not alter the desired metals concentration in the impregnation solution and deposited on the carrier. Organic bases will not alter the impregnation solution metals concentrations, examples of which are tetraalkylammonium hydroxides and 1,8-bis-(dimethylamino)-naphthalen. If changing the metals concentration of the impregnation solution is not a concern, metal hydroxides may be used.

When the impregnation solution is at least partially aqueous, an indication of the change in the hydrogen activity may be measured with a pH meter, with the understanding that the measurement obtained is not pH by a true, aqueous definition. "'Measured pH'" as used herein shall mean such a non-aqueous system pH measurement using a standard pH probe. Even small changes in the "measured pH" from the initial impregnation solution to that with added base are effective and improvements in catalytic properties continue as the "measured pH" change increases with base addition. High base additions do not seem to adversely affect catalyst performance; however, high additions of hydroxides have been seen to cause sludging of the impregnation solution, creating manufacturing difficulties. When the base addition is too low, the hydrogen ion activity will not be affected.

As described, the process is effective in improving at least one of the catalytic properties of catalyst wherein an impregnating solution is used to deposit or impregnate a catalytically reactive metal upon a carrier. "Improvement in catalytic properties" as used herein means the properties of the catalyst are improved as compared to a catalyst made from the same impregnation solution which has not had the hydrogen ion activity lowered. Catalytic properties include catalyst activity, selectivity, activity and/or selectivity performance over time, operability (resistance to runaway), conversion and work rate.

Further improvement in properties may be achieved by lowering the concentration of ionizable species present on the surface of the carrier prior to the deposition step. Carriers are commonly inorganic materials such as refractory inorganic materials, for example alumina-, silica-, or titania-based compounds, or combinations thereof, such as alumina-silica carriers. Carriers may also be made from carbon-based materials such as, for example, charcoal, activated carbon, or fullerenes. Ionizable species typically present on the inorganic type carriers include sodium, potassium, aluminates, soluble silicate, calcium, magnesium, aluminosilicate, cesium, lithium, and combinations thereof. Lowering the undesirable ionizable species concentration may be accomplished by any means (i) which is effective in rendering the ionizable species ionic and removing that species, or (ii) which renders the ionizable species insoluble, or (iii) which renders the ionizable species immobile; however, use of aggressive medias, such as acids or bases, is discouraged as these media tend to dissolve the carrier, extract too much material from the bulk, and generate acidic or basic sites in the pores. Effective means of lowering concentration include washing the carrier; ion exchange; volatilizing, precipitating, or sequestering the impurities; causing a reaction to make the ionizable species on the surface insoluble; and combinations thereof. Examples of wash and ion exchange solutions include aqueous and/or organic solvent-based solutions which may also contain tetraethylammonium hydroxide, ammonium acetate, lithium carbonate, barium acetate, strontium acetate, crown ether, methanol, ethanol, dimethylformamide, and mixtures thereof. The formed carrier may be treated, or the materials used to form the carrier may be treated before the carrier is manufactured. When the carrier materials are treated before the carrier is formed, still further improvement may be seen by retreating the surface of the formed carrier. Following removal of the ionizable species, the carrier is optionally dried. When the removal process is by washing with an aqueous solution drying is recommended.

By way of example, the process will be described in more detail for a catalyst suitable for the vapor phase production of epoxides, also known as an epoxidation catalyst.

First, a carrier is selected, in the case of an epoxidation the carrier is typically an inorganic material, such as, for example, an alumina-based carrier such as α-alumina. The carrier is typically impregnated with metal compound(s), complex(es) and/or salt(s) dissolved in a suitable solvent sufficient to cause the desired deposition on the carrier. If excess of impregnation solution is used, the impregnated carrier is subsequently separated from the impregnation solution and the deposited metal compound is reduced to its metallic state. In the process of the invention, the hydrogen ion activity of the impregnation solution is lowered prior to beginning the deposition or impregnation process. The typical known impregnation solution for an epoxidation catalyst is quite basic, so in accordance with the present invention a strong base may be used to further lower the hydrogen ion activity. It is particularly desirable to chose a base which does not alter the formulation of the impregnation solution, such as organic bases; however, if changing the metals concentration of the impregnation solution is not a concern, metal bases may be used. Examples of strong bases include alkylammonium-hydroxides, such as tetraethylammonium hydroxide, and metal hydroxides, such as lithium hydroxide and cesium hydroxide. Combinations of bases may also be used. In order to maintain the desired impregnation solution formulation and metal loading, an organic base such as tetraethylammonium hydroxide is preferred. These desired level of base additions typically result in a "measured pH" change ranging from about 0.5 to about 3, realizing that the "measured pH" may not be a true pH when the impregnation system is not aqueous. Typically the hydrogen ion activity is lowered such that the "measured pH" is above 11.2, more typically at least about 11.7, preferably at least about 12.0. Typically the hydrogen ion activity is lowered such that the "measured pH" is at most about 14.2, more typically at most about 13.7. As defined herein, "pH" is deemed to relate to pH measured at 20° C.

If an excess of impregnation solution is used, the impregnated carrier is subsequently separated from the solution before the deposited metal compound is reduced. Promoters, components which work effectively to provide an improvement in one or more of the catalytic properties of the catalyst when compared to a catalyst not containing such components, may also be deposited on the carrier either prior to, coincidentally with, or subsequent to the deposition of the catalytically reactive metal.

If the above described ionizable species concentration lowering step is utilized, the concentration of the ionizable species present on the carrier surface is lowered prior to the deposition or impregnation step. Ionizable species present on an α-alumina carrier, for example, typically include sodium, potassium, aluminates, soluble silicates, calcium, magnesium, aluminosilicates, and combinations thereof. It has been found that silicates, and certain other anions, are particularly undesirable ionizable species in an epoxidation catalyst. The solubilization rate of silicates may be measured by inductively coupled plasma (ICP) techniques and the amount of silicon species on a surface may be measured by x-ray photoelectron spectroscopy (XPS); however, since sodium is soluble in the same solutions that silicates are soluble in, the solubilization rate of sodium becomes a simpler check of the ionic species removal. Another measurement technique is to measure the electrical conductivity of the treatment solution.

The concentration of the undesirable ionizable species may lowered by any means which is effective in rendering the ionizable species ionic and removing that species, or rendering the ionizable species insoluble, or rendering the ionizable species immobile. Means effective in lowering the concentration of the undesirable ionizable species on the surface include washing, ion exchange, volatilization, precipitation, sequestration, impurity control and combinations thereof. Cleansing of an alumina-based carrier may be efficiently and cost-effectively accomplished by washing or ion exchange. Any solution capable of reducing the concentration of the undesirable ionizable species present, particularly the anionic ionizable species, and most particularly ionizable silicates, may be used. The carrier is then optionally dried; however, when the removal process is by washing, drying is recommended.

Promoters may also be deposited on the carrier either prior to, coincidentally with, or subsequent to the deposition of the metal(s). As used herein, the term "promoter" refers to a component which works effectively to provide an improvement in one or more of the catalytic properties of the catalyst when compared to a catalyst not containing such component. Promoters are typically compound(s) and/or salt(s) of alkali metal which are optionally deposited on the carrier either prior to, coincidentally with, or subsequent to the deposition of the catalytically reactive metal. Promoters may include, for example, sulfur, phosphorus, boron, fluorine, Group IA through Group VIII metals, rare earth metals, and combinations thereof.

The carrier having the controlled solubilization rate is impregnated with metal ions or compound(s), complex(es) and/or salt(s) dissolved in a suitable solvent sufficient to cause the desired deposition on the carrier. When silver is the deposition material, a typical deposition is from about 1 to about 40 percent by weight, preferably from about 1 to about 30 percent by weight silver, basis the weight of the total catalyst. The impregnated carrier is subsequently separated from the solution and the deposited metal(s) compound is reduced to metallic silver.

One or more promoters may be deposited either prior to, coincidentally with, or subsequent to the deposition of the metal. Promoters for epoxidation catalysts are typically selected from sulfur, phosphorus, boron, fluorine, Group IA through Group VIII metals, rare earth metals, and combinations thereof. The promoter material is typically compound(s) and/or salt(s) of the promoter dissolved in a suitable solvent.

For olefin epoxidation catalysts, Group IA metals are typically selected from potassium, rubidium, cesium, lithium, sodium, and combinations thereof; with potassium and/or cesium and/or rubidium being preferred. Even more preferred is a combination of cesium plus at least one additional Group IA metal, such as cesium plus potassium, cesium plus rubidium, or cesium plus lithium. Group IIA metals are typically selected from magnesium, calcium, strontium, barium, and combinations thereof, Group VIII transition metals are typically selected from cobalt, iron, nickel, ruthenium, rhodium, palladium, and combinations thereof; and rare earth metals are typically selected from lanthanum, cerium, neodymium, samarium, gadolinium, dysprosium, erbium, ytterbium, and mixtures thereof. Non-limiting examples of other promoters include perrhenate, sulfate, molybdate, tungstate, chromate, phosphate, borate sulfate anion, fluoride anion, oxyanions of Group IIIB to VIB, oxyanions of an element selected from Groups III through VIIB, alkali(ne) metal salts with anions of halides, and oxyanions selected from Groups IIIA to VIIA and IIIB through VIIB. The amount of Group IA metel promoter is typically in the range of from about 10 ppm to about 1500 ppm, expressed as the metal, by weight of the total catalyst, and the Group VIIb metal is less than about 360 ppm, expressed as the metal, by weight of the total catalyst.

Other embodiments of the invention provide catalysts made by the processes just described.

The resulting epoxidation catalysts just described are used for the vapor phase production of epoxides. A typical epoxidation process involves loading catalysts into a reactor. The feedstock to be converted, typically a mixture of ethylene, oxygen, carbon dioxide, nitrogen and ethyl chloride, is passed over the catalyst bed at pressure and temperature. The catalyst converts the feedstock to an outlet stream product which contains ethylene oxide. Nitrogen oxides ($NO_x$) may also be added to the feedstock to boost catalyst conversion performance.

Having generally described the invention, a further understanding may be obtained by reference to the following examples, which are provided for purposes of illustration only and are not intended to be limiting unless otherwise specified.

EXAMPLES

Carriers

The properties of the carriers used in the Examples are given in Table I.

TABLE I

| Carrier | A | B |
|---|---|---|
| B.E.T. Surface Area ($m^2/g$)[a] | 0.84 | 0.97 |
| Water Absorption (%) | 39.7 | 46.2 |
| Crush Strength (kg)[b] | 6.53 | 8.07 |
| Total Pore Volume (cc/g)[c] | 0.408 | 0.460 |
| Median Pore Diameter (microns)[c] | 1.8 | 2.7 |
| $SiO_2$ (% w) | 0.5 | 0.8 |
| Bulk Acid-Leachable Na (ppmw) | 438 | 752 |
| Bulk Acid-Leachable K (ppmw) | 85 | 438 |
| Bulk Acid-Leachable Ca (ppmw) | 207 | 508 |
| Bulk Acid-Leachable Al (ppmw) | 744 | 1553 |
| Bulk Acid-Leachable $SiO_2$ (ppmw) | 808 | 1879 |
| alpha-Alumina (% w) | Bal | Bal |

[a]Method of Brunaner, Emmett and Teller, loc. cit.
[b]Flat Plate Crush Strength, single pellet.
[c]Determined by mercury intrusion to $3.8 \times 10^8$ Pa using Micromeritics Autopore 9200 or 9210 (130° contact angle, 0.473 N/m surface tension of Hg).

Carrier Washing Procedures for Examples 1, 3, 4, 5, 6, 7, 8, 9, 10, 12

Carrier washing was carried out by immersing 100 grams of carrier in 300 grams of boiling de-ionized water for 15 minutes. The carrier was then removed and placed in a fresh 300 grams of boiling water for another 15 minutes. This procedure was repeated once more for a total of three immersions, at which point the carrier was separated from the water and dried in a well ventilated oven at 150° C. for 18 hours. The dried carrier was then used for preparation of a catalyst by the procedures outlined in the following Examples.

Impregnation Solution

A silver-amine-oxalate stock solution was prepared by the following procedure:

415 g of reagent-grade sodium hydroxide were dissolved in 2340 ml de-ionized water and the temperature was adjusted to 50° C.

1699 g high purity "Spectropure" silver nitrate were dissolved in 2100 ml de-ionized water and the temperature was adjusted to 50° C.

The sodium hydroxide solution was added slowly to the silver nitrate solution, with stirring, while maintaining a solution temperature of 50° C. The mixture was stirred for 15 minutes, then the temperature was lowered to 40° C.

Water was removed from the precipitate created in the mixing step and the conductivity of the water, which contained sodium and nitrate ions, was measured. An amount of fresh deionized water equal to the amount removed was added back to the silver solution. The solution was stirred for 15 minutes at 40° C. The process was repeated until the conductivity of the water removed was less than 90 $\mu$mho/cm. 1500 ml fresh deionized water was then added.

630 g of high-purity oxalic acid dihydrate were added in approximately 100 g increments. The temperature was keep at 40° C. and the pH was kept above 7.8.

Water was removed from the mixture to leave a highly concentrated silver-containing slurry. The silver oxalate slurry was cooled to 30° C 699 g of 92% w ethylenediamine (8% de-ionized water) was added while maintaining a temperature no greater than 30° C. The resulting solution contained approximately 27–33% w silver.

Enough 45% w aqueous CsOH and water was added to this solution to give a finished catalyst having 14.5% w silver and a desired cesium loading (see Examples).

pH Measurement Procedures

Silver solution pH measurements were done using a Metrohm model 744 pH meter, employing a model 6.0220.100 combination electrode and a Pt 100 model 6.1110.100 resistance thermometer for temperature compensation. The meter was calibrated with commercially available buffer solutions before each use. In a typical measurement, a 50 cc aliquot of the doped silver solution to be used for a catalyst impregnation was filtered into a 100 cc glass beaker through a 2 micron filter attached in-line to a plastic syringe. The pH probe was lowered into the magnetically stirred solution, and the reading obtained after 3 minutes was recorded as the equilibrated pH. The probe was cleaned between each measurement with deionized water, and checked for calibration. Special care was taken to prevent accumulation of AgCl solids on the electrode membrane. Such accumulation was removed by soaking the probe in ammonium hydroxide solution, as recommended by the manufacturer.

Example 1

Comparative—Base Case Carrier A, Washing

A catalyst pre-cursor was prepared from Carrier A by first subjecting the carrier to carrier washing. Following the wash, approximately 30 grams of washed Carrier A were placed under a 25 mm Hg vacuum for 1 minute at ambient temperature. Approximately 50 grams of the impregnating solution was then introduced to submerse the carrier, and the vacuum was maintained at 25 mm Hg for an additional 3 minutes. The cesium target was 450 ppm/gram finished catalyst. The vacuum was then released and the excess impregnating solution was removed from the catalyst pre-cursor by centrifugation at 500 rpm for two minutes. The catalyst pre-cursor was then dried while being shaken at 240° C. for 4 minutes in a stream of air flowing at 11.3 m$^3$/hr.

Example 2

Comparative—Base Case Carrier A, No Washing

Carrier A was impregnated as described in Example 1; however, the carrier was not subjected to carrier washing. The cesium target was 400 ppm/gram finished catalyst.

Example 3

Carrier A was subjected to carrier washing and impregnation as described in Example 1. The cesium target was 500 ppm/gram finished catalyst. In addition, 35% aqueous tetraethylammonium hydroxide (TEAH) was added to the stock impregnation solution at a target of 117.8 micromoles OH$^-$/cc Ag solution, to lower the hydrogen ion activity to a "measured pH" of 13.7.

Example 4

A catalyst was prepared in the same manner as that in Example 1. The cesium target was 720 ppm/gram finished catalyst. In addition, TEAH was dissolved in water and added to the stock solution at a target of 117.8 micromoles OH$^-$/cc Ag, to lower the hydrogen activity to a "measured pH" of 13.2, and NH$_4$ReO$_4$ was dissolved in water and added to the stock solution to provide 1.5 micromoles Re/gram finished catalyst.

Example 5

500 g of Carrier A were subjected to carrier washing then immersed in 1500 ml of boiling 5% w aqueous TEAH for 15 minutes. The carrier was then separated from the solution and washed repeatedly with boiling water according to the Carrier Washing Procedure. The carrier was then used to prepare a catalyst according to the procedure described in Example 2 with a "measured pH" of 13.6. The cesium target was 400 ppm/gram finished catalyst.

Example 6

Carrier A was subjected to carrier washing and impregnation as described in Example 1. The cesium target was 430 ppm/gram finished catalyst. In addition, LiNO$_3$ and LiOH were added to the stock impregnation solution, lowering the hydrogen ion activity to a "measured pH" of 12.5.

Example 7

Carrier A was subjected to carrier washing and impregnation as described in Example 1. The cesium target was 450 ppm/gram finished catalyst. In addition, LiOH was dissolved in water and added to the stock impregnation solution to lower the hydrogen ion activity to a "measured pH" of 13.2.

Example 7a

Carrier A catalyst was impregnated as described in Example 7; however, the carrier was not subjected to carrier washing. The cesium target was 400 ppm/gram finished catalyst.

Example 8

A silver solution was prepared as described in Example 7. The "measured pH" of the solution was 13.2. CO$_2$ was bubbled slowly through the solution until the "measured pH" was 12.0. The solution was used to prepare a catalyst as described in Example 1.

Example 9

A catalyst was prepared in the same manner as that in Example 1. The cesium target was 650 ppm/gram finished catalyst. In addition, LiOH was dissolved in water and added to the stock impregnation solution to lower the hydrogen ion activity to a "measured pH" of 13.2 and NH$_4$ReO$_4$ was dissolved in water and added to the stock impregnation solution to provide 1.5 micromoles Re/gram finished catalyst.

Example 10 (Comparative—Base Case Carrier B, Washing)

Carrier B was used to prepare a catalyst as described in Example 1. The cesium target was 450 ppm/gram catalyst.

Example 11

Comparative—Base Case Carrier B, No Washing

Carrier B was impregnated as described in Example 1; however, the carrier was not subjected to carrier washing. The cesium target was 500 ppm/gram finished catalyst.

Example 12

Carrier B was used to prepare a catalyst as described in Example 1. The cesium target was 550 ppm/gram finished catalyst. In addition, LiOH was dissolved in water and added to the stock impregnation solution to lower the hydrogen ion activity to a "measured pH" of 13.2.

Example 12a

A catalyst was prepared as described in Example 12; however, the carrier was not subjected to carrier washing. The cesium target was 500 ppm/gram finished catalyst.

The catalysts of Examples 1–12a were used to produce ethylene oxide from ethylene and oxygen. 3 to 5 grams of crushed catalyst were loaded into a 6.35 mm inside diameter stainless steel U-shaped tube. The U tube was immersed in a molten metal bath (heat medium) and the ends were connected to a gas flow system. The weight of the catalyst used and the inlet gas flow rate were adjusted to achieve a gas hourly space velocity of 6800 cc of gas per cc of catalyst per hour. The inlet gas pressure was 1450 kPa.

The gas mixture passed through the catalyst bed (in a once-through operation) during the entire test run (including start-up) consisted of 25% ethylene, 7.0% oxygen, 5% carbon dioxide, 63% nitrogen, and 2.0 to 6.0 ppmv ethyl chloride.

The initial reactor (heat medium) temperature was 180° C. The temperature was ramped at a rate of 10° C. per hour from 180° C. to 225° C., and then adjusted so as to achieve a constant ethylene oxide level of 1.5% v in the outlet gas stream. Performance data at this conversion level are usually obtained when the catalyst has been on stream for a total of at least 1–2 days. Due to slight differences in feed gas composition, gas flow rates, and the calibration of analytical instruments used to determine the feed and product gas compositions, the measured selectivity and activity of a given catalyst may vary slightly from one test run to the next.

The initial performance values for selectivity at 1.5% ethylene oxide were measured and are reported in Table II.

TABLE II

Performance Characteristics of Catalysts

| Example | Carrier | Pre-Impregnation Condition | Base Addition | Impregnating Solution "measured pH" | Selectivity (%) | Temperature (° C.) |
|---|---|---|---|---|---|---|
| 1 | A | Water wash | none | 11.2 | 82.7 | 229 |
| 2 | A | no wash | none | 11.2 | 81.3 | 237 |
| 3 | A | Water wash | TEAH | 13.7 | 82.7 | 225 |
| 4 | A | Water wash | TEAH | 13.2 | 89.4 | 245 |
| 5 | A | TEAH wash + Water wash | TEAH | 13.6 | 82.7 | 222 |
| 6 | A | Water wash | LiNO$_3$ + LiOH | 12.5 | 82.7 | 225 |
| 7 | A | Water wash | LiOH | 13.2 | 82.7 | 227 |
| 7a | A | no wash | LiOH | 13.2 | 82.0 | 227 |
| 8 | A | Water wash | LiOH + CO$_2$ | 12.0 | 82.8 | 231 |
| 9 | A | Water wash | LiOH | 13.2 | 86.2 | 234 |
| 10 | B | Water wash | none | 11.2 | 82.5 | 226 |
| 11 | B | no wash | none | 11.2 | 82.0 | 232 |
| 12 | B | Water wash | LiOH | 13.2 | 82.9 | 226 |
| 12a | B | no wash | LiOH | 13.2 | 83.3 | 230 |

It can be seen that significant improvement in catalyst properties are seen when the hydrogen ion activity of the deposition solution is lowered. This effect is not specific for a certain carrier, as illustrated in the Example where two different carriers exhibit improvements by increasing "measured pH" of the impregnating solution. This also holds true for a drastically modified carrier, as in Example 5, where Carrier A has been extracted with a strongly basic solution. Furthermore, the converse is shown to be true when the solution is "forced" back to a more acidic pH, as seen in Example 8. In these examples it is shown that a more acidic pH (increasing hydrogen ion activity) is detrimental to the resulting catalyst performance, but this loss can be reversed by rejuvenating the pH of the system. Even further improvement is seen when the carrier is washed before the catalytic metal is deposited on the carrier. It is also evident that the phenomenon of the pH effect is not restricted to a particular catalyst formulation, as best illustrated in Examples 4 and 9, where a selectivity enhancing dopant, such as rhenium, is added to the impregnating solution.

It will be apparent to one of ordinary skill in the art that many changes and modifications may be made to the invention without departing from its spirit or scope as set forth herein.

I claim:

1. A process for depositing one or more catalytically reactive metals comprising silver on a carrier, said process comprising:
   selecting a carrier which is a refractory inorganic carrier; and
   depositing a catalytically effective amount of one or more catalytically reactive metals comprising silver on the carrier, said deposition effected by an impregnation solution wherein prior to beginning the deposition a hydrogen ion activity of said impregnation solution is lowered to a pH of above 11.2.

2. A process according to claim 1 wherein said hydrogen ion activity is lowered to a pH in the range of from about 11.7 to 14.2.

3. A process according to claim 1 wherein said hydrogen ion activity is lowered by addition of a base.

4. A process according to claim 3 wherein said base is a base selected from metal hydroxides, tetraalkylammonium hydroxides and 1,8-bis(dimethylamino)naphthalene.

5. A process according to claim 1 wherein said refractory inorganic carrier is an alumina-, silica-, or titania-based compounds, or a combination thereof.

6. A process according to claim 1 further comprising lowering a concentration of one or more ionizable species present on a surface of said carrier prior to said deposition step.

7. A process according to claim 6 wherein said concentration of one or more ionizable species is lowered by a means effective in rendering the ionizable species ionic and removing that species, or rendering the ionizable species insoluble, or rendering the ionizable species immobile.

8. A process according to claim 7 wherein said means is selected from washing, ion exchange, volatilization, precipitation, sequestration and combinations thereof.

9. A process according to claim 8 wherein said concentration of one or more ionizable species is lowered by washing with an aqueous and/or organic solvent-based solution.

10. A process for preparing a catalyst suitable for the vapor phase production of epoxides, said process comprising:
    selecting a carrier which is a refractory inorganic carrier; and
    depositing a catalytically effective amount of silver on said carrier, said deposition effected by submersing said carrier in an impregnation solution wherein prior to beginning the deposition a hydrogen ion activity of said impregnation solution is lowered to a pH of above 11.2.

11. A process according to claim 10 wherein said hydrogen ion activity is lowered to a pH in the range of from about 11.7 to 14.2.

12. A process according to claim 10 wherein said hydrogen ion activity is lowered by addition of a base.

13. A process according to claim 12 wherein said base is a base selected from metal hydroxides, tetraalkylammonium hydroxides and 1,8-bis(dimethylamino)naphthalene.

14. A process according to claim 12 wherein said refractory inorganic carrier is an alumina-, silica-, or titania-based compounds, or a combination thereof.

15. A process according to claim 10 further comprising lowering a concentration of one or more ionizable species present on a surface of said carrier and optionally drying said carrier prior to said deposition step.

16. A process according to claim 15 wherein said concentration of said one or more ionizable species is lowered by a means effective in rendering the ionizable species ionic and removing that species, or rendering the ionizable species insoluble, or rendering the ionizable species immobile.

17. A process according to claim 16 wherein said means is selected from washing, ion exchange, volatilization, precipitation, sequestration and combinations thereof.

18. A process according to claim 17 wherein said concentration of one or more ionizable species is lowered by washing with an aqueous and/or organic solvent-based solution.

19. A process according to claim 18 wherein said aqueous and/or organic solvent-based solution is selected from water, tetraethylammonium hydroxide, ammonium acetate, lithium carbonate, barium acetate, strontium acetate, crown ether, methanol, ethanol, dimethylformamide, and mixtures thereof.

20. A process according to claim 18 further comprising depositing one or more promoters selected from sulfur, phosphorus, boron, fluorine, Group IA through Group VIII metals, rare earth metals, and combinations thereof.

21. A process according to claim 20 wherein said carrier is an alumina-based carrier.

22. A process according to claim 21 wherein said Group IA metal is selected from potassium, rubidium, cesium, lithium, sodium, and combinations thereof.

23. A process according to claim 21 wherein Group IIA metal is selected from magnesium, calcium, strontium, barium, and combinations thereof.

24. A process according to claim 21 wherein said Group VIIb metal is rhenium.

25. A process according to claim 21 wherein said Group VIII metal is selected from cobalt, iron, nickel, ruthenium, rhodium, palladium, and combinations thereof.

* * * * *